US007564201B2

(12) United States Patent
Steckling (10) Patent No.: US 7,564,201 B2
(45) Date of Patent: Jul. 21, 2009

(54) INTELLIGENT GAS DISCHARGE LAMP CONTROL CIRCUIT

(75) Inventor: Philip J. Steckling, San Luis Obispo, CA (US)

(73) Assignee: Clearwater Technology, LLC, San Luis Obispo, CA (US)

( * ) Notice: Subject to any disclaimer, the term of this patent is extended or adjusted under 35 U.S.C. 154(b) by 546 days.

(21) Appl. No.: 11/462,682

(22) Filed: Aug. 4, 2006

(65) Prior Publication Data

US 2008/0030144 A1 Feb. 7, 2008

(51) Int. Cl.
*H05B 37/02* (2006.01)

(52) U.S. Cl. .................. 315/312; 315/224; 315/307; 315/308

(58) Field of Classification Search .................. 315/312, 315/313, 314, 315, 291, 307, 308, 224, DIG. 5
See application file for complete search history.

(56) References Cited

U.S. PATENT DOCUMENTS

| | | | |
|---|---|---|---|
| 4,942,046 | A | 7/1990 | Scott |
| 5,001,400 | A | 3/1991 | Nilssen |
| 5,106,589 | A | 4/1992 | Conrad |
| 5,540,898 | A | 7/1996 | Davidson |
| 5,547,590 | A | 8/1996 | Szabo |
| 5,907,222 | A | 5/1999 | Lengyel et al. |
| 6,188,179 | B1 | 2/2001 | Boys et al. |
| 6,461,520 | B1 | 10/2002 | Engelhard et al. |
| 6,569,319 | B2 | 5/2003 | Kuennen et al. |
| 6,954,038 | B2 * | 10/2005 | Ido et al. ............... 315/291 |
| 7,126,288 | B2 * | 10/2006 | Ribarich et al. ......... 315/308 |
| 2004/0061069 | A1 | 4/2004 | Schalble et al. |

FOREIGN PATENT DOCUMENTS

GB 2319406 A 5/1998

OTHER PUBLICATIONS

Electronic Ballasts Using the Cost-Saving IR215X Drivers AN-995A, International rectifiers.
FAN7544 Simple Ballast Controller,2004 Fairchild Semiconductor Corporation.
IR2156(S) & (PbF); Ballast Control IC; Data Sheet No. PD60182-International rectifier.

(Continued)

*Primary Examiner*—David Hung Vu
(74) *Attorney, Agent, or Firm*—Gunnison, McKay & Hodgson, L.L.P.

(57) ABSTRACT

An electronic control circuit for intelligently controlling a gas discharge lamp associated with an HVAC system. The circuit includes a microcontroller having a memory containing instructions executable by the microcontroller to process a plurality of dynamic lamp state signals and dynamically generate control signals in at least partial dependence on a plurality of pre-established control parameters to maintain the gas discharge lamp in a minimum operable state defined by the pre-established control parameters. The gas discharge lamp is coupled to an electronic ballast circuit configured to dynamically control a current flow through the gas discharge lamp in dependence on the dynamically generated control signals sent by the microcontroller. The executable instructions cause the microcontroller to iteratively determine the minimum operable state of the gas discharge tube in at least partial dependence on a voltage excursion included as one of the plurality of dynamic lamp state signals.

28 Claims, 4 Drawing Sheets

OTHER PUBLICATIONS

IR21592(S) IR21593(S); Dimming Ballast Control IC;Data Sheet No. PD60194_A; International Rectifier.
International Rectifier Announces Phase Control Loop Ballast ICs to Achieve Transformer-Less Dimming.
MC34262, MC33262; Power Factor Controllers;Semiconductor Components Industries, LLC, 2005.
ComAir 20T ClearWater Technologies, LLC.

* cited by examiner

INTELLIGENT GAS DISCHARGE LAMP CONTROL CIRCUIT

CROSS-REFERENCE TO RELATED APPLICATIONS

Not Applicable

FEDERALLY SPONSORED RESEARCH AND DEVELOPMENT

Not Applicable

REFERENCE TO A MICROFICHE APPENDIX

Not Applicable

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

RELEVANT FIELD

A electronic control circuit is described for implementation in a heating, ventilating, and air conditioning (HVAC) system; and more specifically, an electronic control circuit for intelligently controlling a plurality of gas discharge lamps used in the environmental and biocidal treatment of air.

BACKGROUND

Electronic ballasts have significant advantages over inductive type ballasts known in the relevant art; including greater energy efficiency, smaller size, lower cost and lower component and maintenance costs. Many of the electronic ballasts allow for electrical programming of the lamp's various operating parameters by selecting components that provide an RC time constant of a proper frequency for the various types of the gas discharge lamps to be connected to the electronic ballasts.

The selected components are then hardwired to the electronic ballasts and are not changed for the life of the electronic ballast circuits. The criteria for selecting the proper resistors and capacitors are based on the lamp's manufacturer recommendations. The operating characteristics of the gas discharge lamps used in selecting the components are optimized by the manufactures for maximum energy efficiency for a new or "typical" lamp.

However, the operating characteristics for a given type of gas discharge lamp may vary among manufacturers, change over time as the lamps are used and vary according to their environmental conditions. A selected operating program for a new or "typical" gas discharge lamp may be deleterious to a lamp after a given amount of operating time which adversely impacts the life of the lamp, increases maintenance costs and downtime, and may increase hazardous waste generation as many gas discharge lamps contain sufficient quantities of mercury to require disposal as hazardous waste or otherwise require special handling for recycling purposes. Therefore, a simple mechanism to intelligently control the operating characteristics of a gas discharge lamp over time would be advantageous.

SUMMARY

This disclosure addresses the deficiencies of the relevant art and provides in various embodiments an electronic control circuit for intelligently controlling a gas discharge lamp associated with an HVAC system.

In a first main exemplary embodiment, the electronic control circuit comprises a microcontroller operatively coupled to a memory. The memory includes instructions executable by the microcontroller to process a plurality of dynamic lamp state signals and dynamically generate control signals in at least partial dependence on a plurality of pre-established control parameters. The pre-established control parameters facilitate the maintenance of the gas discharge lamp in a minimum operable state defined by the pre-established control parameters under dynamically varying environmental conditions. An electronic ballast circuit is used to dynamically control a current flow through the gas discharge lamp in dependence on the dynamically generated control signals. The microcontroller iteratively determines the minimum operable state of the gas discharge tube in at least partial dependence on a voltage excursion included as one of the plurality of dynamic lamp state signals.

In a first related exemplary embodiment, an airflow sensor is operatively coupled to the microcontroller and configured to provide airflow state signals to the microcontroller based on airflow detected in the HVAC system.

In a second related embodiment, the airflow sensor is configurable to control one of: the biocide lamp, ozone generation lamp and any combination thereof in dependence on various airflow thresholds to compensate for dynamic air flow variations.

In a third related exemplary embodiment, an ozone sensor is operatively coupled to the microcontroller. The ozone sensor provides ozone sensor signals to the microcontroller in based on detected ozone concentrations in the HVAC system.

In a fourth related exemplary embodiment, a power supply configured to provide sufficient electrical power to the microcontroller, electronic ballast circuit and the gas discharge lamp in an isolated ground arrangement such that voltage measurements are relative to a negative portion of an input power sine wave.

In a fifth related exemplary embodiment, a user interface is operatively coupled to the microcontroller. The user interface is configured to receive user inputs which allow a user to manually override the microcontroller. In addition, the user interface displays a state of the airflow sensor, the gas discharge lamp, the ozone sensor, the power supply and a current control mode.

In a sixth related exemplary embodiment, the dynamic control signals may include an IN/OUT signal, a pulse width modulation output signal, an output intensity signal, a user interface signal, a current sense signal and a voltage sense signal.

In a seventh related exemplary embodiment, the plurality of dynamic states of the gas discharge lamp may include an ON state, an OFF state, a preheat state, an ignition state, and a dimmed state.

In an eighth exemplary related embodiment, the dynamic lamp state signals are 0-5 volt signals measured relative to a negative portion of an input power sine wave and an isolated ground.

In a ninth exemplary related embodiment, the plurality of pre-established control parameters may include operating cycle time(s), an output intensity level, a low ozone setpoint, a scheduled service interval, and a high ozone setpoint.

In a tenth related exemplary embodiment, the low and high setpoints may include a voltage, a current, an ozone concentration and a pulse width modulation frequency.

In a twelfth eleventh related exemplary embodiment, the voltage excursion is measured relative to a negative portion of an input power sine wave and an isolated ground.

In a thirteenth related exemplary embodiment, the output intensity level may controlled to about a 25 percent output intensity with a 50% duty cycle of the gas discharge tube in a low mode, about 50 percent output intensity in a medium mode mode, 75 percent output intensity in a high mode and 100 percent output intensity in a boost mode.

In a fourteenth related exemplary embodiment, the ozone sensor signals may include a 4-20 ma current signal, 0-5V voltage signal and an ON/OFF state signal.

In a fifteenth related exemplary embodiment, the output intensity may be dynamically controlled at 256 discrete levels in a range corresponding to 50% to 100%.

In a sixteenth related exemplary embodiment, the output intensity may be dynamically controlled at output levels below 50% by pulsing of the gas discharge lamp.

In a seventh related exemplary embodiment, the instructions executable by the microcontroller further includes executable instructions to adjust a voltage excursion detection sensitivity in at least partial dependence one or more of the plurality of pre-established control parameters.

In a second main exemplary embodiment, an electronic control circuit for intelligently controlling a pair of gas discharge lamps associated with an HVAC system is provided. This second exemplary embodiment comprises a microcontroller including a memory having instructions executable by the microcontroller to dynamically generate control signals in at least partial dependence on a plurality of optically isolated sensor signals and voltage input signals.

The microcontroller also has functionally coupled to it, first and second electronic ballasts. The first ballast is configured to control a first current flow through an ozone generation lamp in dependence on a portion of the dynamically generated control signals. The second ballast is configured to control a second current flow through a biocide lamp in dependence on another portion of the dynamically generated control signals.

In a first related exemplary embodiment, the plurality of input signals includes a voltage signal derived from an operational state dependent voltage applied to the ozone generation lamp.

In a second related exemplary embodiment, the plurality of input signals includes a voltage signal derived from an operational state dependent of the biocide lamp. In a third related exemplary embodiment, the plurality of optically isolated input signals includes user interface signals and sensor signals.

In a fourth related exemplary embodiment, the airflow sensor is configurable to control one of, the biocide lamp, ozone generation lamp and any combination thereof in dependence on various airflow thresholds included in one or more of the plurality of pre-established control parameters to compensate for dynamic air flow variations.

In a third main exemplary embodiment, an electronic control circuit for controlling a pair of disparate gas discharge lamps associated with an HVAC system is provided. This third main exemplary embodiment comprises a microcontroller including a memory having instructions executable by the microcontroller to process a plurality of input signals and dynamically generate control signals for each of the gas discharge lamps in at least partial dependence on a plurality of pre-established control parameters.

The pre-established control parameters facilitate the maintenance of the gas discharge lamps in states defined by the pre-established control parameters. A first electronic ballast circuit is operatively coupled to the microcontroller and configured to control a current flow through either an ozone generation lamp or a first biocide lamp in at least partial dependence on voltage dependent control signals received from the microcontroller. A second electronic ballast circuit is likewise operatively coupled to the microcontroller and configured to control a current flow through a second biocide lamp in at least partial dependence on voltage dependent control signals received from the microcontroller.

In a first related exemplary embodiment, the plurality of input signals includes airflow state signals, ozone sensor signals, current signals, voltage signals and ON/OFF state signals.

In a second related exemplary embodiment, the dynamically generated control signals associated with the ozone generation lamp is generally dependent on the ozone sensor signals.

In a third related exemplary embodiment, the voltage dependent control signals comprises a ground isolated 0-5V signal measured relative to a negative portion of an input power sine wave and the isolated ground.

In a fourth related exemplary embodiment, the dynamically generated control signals derived from the airflow state signals controls both the ozone generation lamp and the biocide lamp.

In a fifth related exemplary embodiment, the ON/OFF state signals is associated with one of, a relay state, electrical power state and a user interface switch.

In a sixth related exemplary embodiment, the ozone generation lamp is iteratively controlled by the microcontroller to maintain operation at a lowest possible operating intensity in at least partial dependence on the plurality of input signals.

In a seventh related exemplary embodiment, the microcontroller ignites the biocide lamp only after a sufficient warm-up period is confirmed by a significant increase in resistance is detected across a filament associated with the biocide lamp and using an electronic ballast circuit lacking an internal dimming circuit.

BRIEF DESCRIPTION OF THE DRAWINGS

The features and advantages will become apparent from the following detailed description when considered in conjunction with the accompanying drawings. Where possible, the same reference numerals and characters are used to denote like features, elements, components or portions. It is intended that changes and modifications can be made to the described exemplary embodiments without departing from the true scope and spirit of the subject invention.

DETAILED DESCRIPTION

An electronic control circuit is described in various embodiments which utilizes a microcontroller under programmatic control to receive and process a plurality of sensor signals derived from electronic ballast circuits, determine the appropriate operational state(s) for one or more gas discharge lamps in dependence on a plurality of pre-established control parameters and the processed sensor signals.

Figure 1:
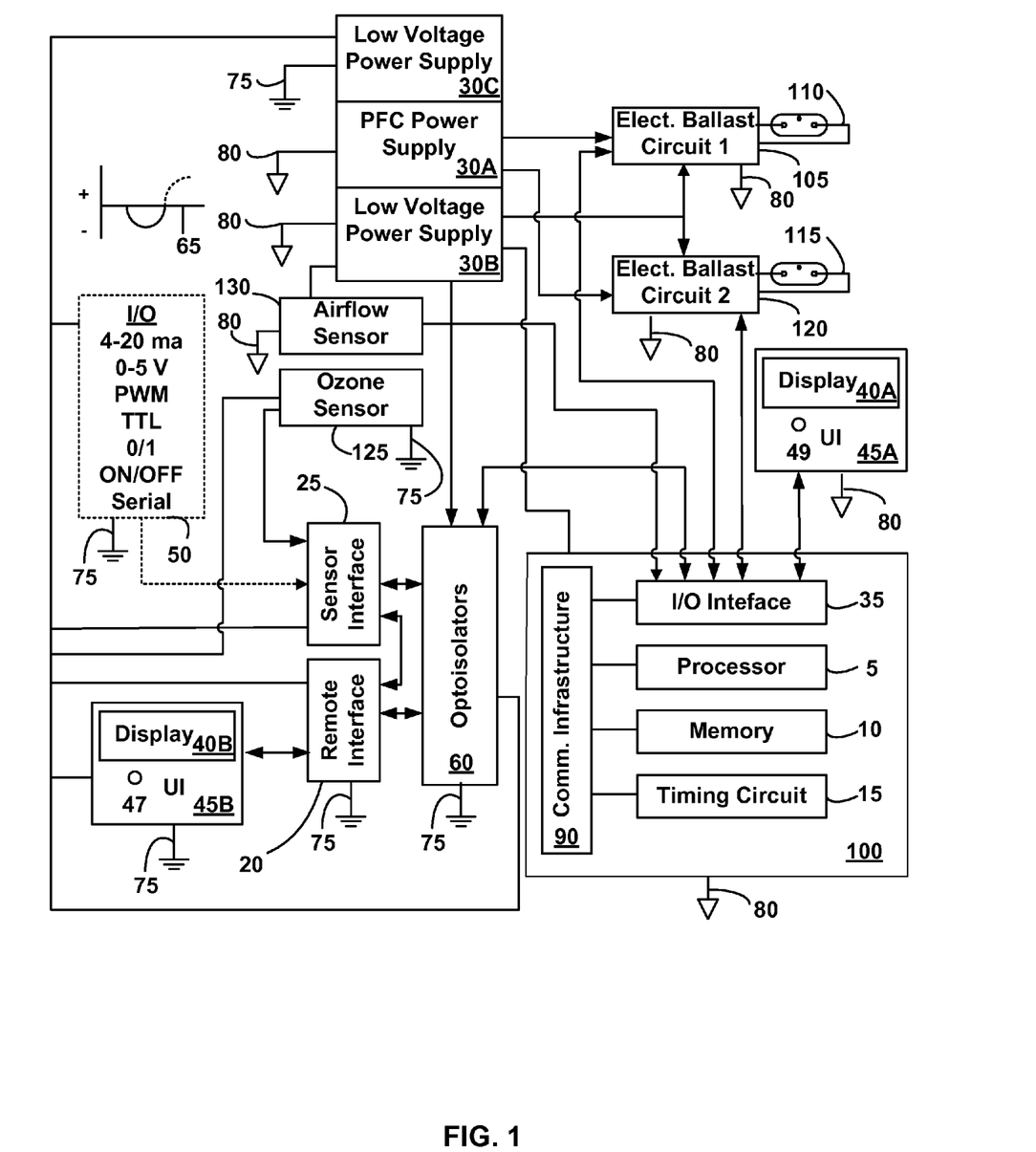
FIG. 1—depicts a generalized and exemplary block diagram of an intelligent electronic control circuit as described in the various exemplary embodiments.

FIG. 1 provides a generalized and exemplary block diagram of an intelligent electronic control circuit as is described in the various exemplary embodiments. The intelligent electronic control circuit includes a microcontroller 100, a pair of electronic ballast circuits 105, 120, and a three part voltage power supply 30A, B, C. Each electronic ballast circuit 105, 120, is designed to power a different type of ultraviolet lamps 110, 115 under the programmatic control of the microcontroller 100. In an embodiment, the electronic ballast circuit 120 is disposed in a modular plug in form factor which allows for the operation of an ozone generation lamp 110 and biocide lamp 115 or two biocide lamps 115'. The electronic ballast circuit 105 for the ozone lamp 110 an internal dimming circuit. The electronic ballast circuit 120 for the biocide lamp 115 does not use an internal dimming circuit which provides additional cost savings over the more expensive internally dimmable electronic ballast circuit 105.

One portion of the power supply 30A provides a highly regulated and power factor corrected output to power the majority of the electronic circuits at approximately 400 VDC relative to the negative portion of the alternating current sine wave 65 and is utilizes an isolated ground 80. The second portion of the power supply 30B utilizes the same isolated (i.e., floating) ground 80 arrangement and provides a 12VDC output relative to the negative portion of the alternating current sine wave 65. The third portion of the power supply 30C provides an 18 VDC output relative to common ground 75 to safely power the remote user interface 45B without electrical shock potential.

The microcontroller 100 is operated using the isolated ground system 80 which allows the microcontroller 100 to simply and directly measure relative voltage changes induced by changes in the operating state (i.e., OFF, PREHEAT, IGNITION, ON) of the ozone generation lamp 110. The isolated ground arrangement 80 places the microcontroller at the same voltage potential as the gas discharge lamps 110, 115 which allows for relative voltage changes to be accurately measured by the microcontroller 100.

The power supply 30A includes circuits to provide for power factor correction and optionally electromagnetic interference attenuation (EMI.)

The microcontroller 100 receives signals to determine the lamp configuration mode of the system (ozone and biocide lamps or two biocide lamps); a current signal from the biocide lamp 115 indicating that the biocide lamp 115 is actually in an ON state; a voltage signal proportional to the ozone generation lamp voltage; user interface 45A, B pushbutton 47, 49 signals; a signal from the ozone sensor 125, a signal from the ground isolated low voltage power supply 30B indicative of a power failure, and a signal from the airflow sensor 130. In an alternate embodiment, the microcontroller 100 determines if an ozone sensor 125 is connected to the microcontroller, and if so, the type ozone sensor 125 (not shown.)

The microcontroller 100 utilizes one or more of these input signals to programmatically control the operation of the two lamps 110, 115. The microcontroller 100 under programmatic control output signals to turn the two lamps 110, 115 ON or OFF; display the operational mode of the control system on the user interface(s) 45A, 45B; and a pulse width modulated (PWM) signal 50 to set the output intensity level of the ozone generation lamp 110. The PWM signal is conditioned back to a 0-5VDC signal to directly interface with the electronic ballast circuits 105, 120.

The microcontroller 100 includes a processor 5, a memory 10, a timing circuit 15, and an I/O interface 35. A suitable microcontroller 100 is available from Microchip Technology, Inc., www.microchip.com, number PIC16F690. The microcontroller 100 is a highly integrated device which incorporates into a single package analog-to-digital conversion circuitry, timing circuitry, communications circuitry, comparator circuitry, multiplexer circuitry, and flash memory circuitry. Information concerning the PIC 16F690 is provided in Microchip Technology, Inc. specification sheet, entitled "PIC 16F685/687/689/690, Data Sheet, 20-Pin Flash-Based, 8-Bit, CMOS Microcontrollers with nanoWatt Technology," 2005, which is herein incorporated by reference.

The microcontroller 100 includes a communications infrastructure 90 used to transfer data, memory addresses where data items are to be found and control signals 50 among the various components and subsystems associated with or coupled to the microcontroller 100. The processor 5 is provided to interpret and execute logical instructions stored in the memory 10.

The memory 10 is the primary general purpose storage area for instructions and data to be processed by the processor 5. The term memory 10 is used in its broadest sense and includes RAM, EEPROM and ROM. The memory 10 maintains the firmware which is executed by the processor 5, a set of predetermined control parameters, variables and other data necessary to intelligently control the operation of the two lamps 110, 115.

A timing circuit 15 is provided to coordinate activities within the processor 5 in near real time and may be used to make time-based assessments of signals received by an I/O interface sensor interface 35.

The I/O interface 35 receives signals from a variety of external electronic circuits including a set of optoisolators 60, a sensor interface 25 and a remote interface 20. The flexible nature of the microcontroller 100 allows the I/O interface 35 to utilize signals provided in a variety of forms including analog, 4-20 milliamps (ma), 0-5 volts (V); pulse width modulation (PWM); transistor to transistor logic (TTL), binary or state, (0/1 and ON/OFF); and serial communications formats. The optoisolators 60 electrically isolate the remote user interface 45B, ozone sensor 125 (if installed) and associated interface circuitry 20, 25 from voltages apparent on the microcontroller 100 due to the isolated ground arrangement. The sensor signals 50 are conditioned backed from PWM signals used to traverse the optoisolators 60 to 0-4.3 VDC signals rather than to 0-5 VDC to protect the microcontroller 100 from over-voltages.

The remote interface circuit 20 is provided to drive a user interface UI 45B which includes a display 40B and a least one pushbutton 47. In its simplest embodiment, the display 40B consists of one or more light emitting diodes (LED). The display 40B and user interface 45B may be integrated into a common housing which allows remote operation of the control system. A local user interface UI 45A is provided for operating the control system at the microcontroller panel, generally during servicing of the control system. The local user interface may include a simple display 40A and one or more pushbuttons 49 analogous to the remote user interface 45B.

The user interfaces 45A, B allow for manually controlling the microcontroller 100 and/or displaying the operating mode of the control system, generally using LEDs 40A, B. The LEDs also provide an indication of the operating status of the various external devices 30, 105, 120, 125, 130 and low voltage power supply 30B. In another embodiment, the displays 40A, B and user interfaces 45A, B may be integrated into a touch sensitive liquid crystal display (LCD) screen. The user interface 45A, B provides the means for a user to control and interact with the microcontroller 100. The user interface 45A, B provides interrupt signals to the processor 5 that may be used to interpret user interactions with the microcontroller 100 and are electrically coupled to the communications infrastructure 90 via the I/O interface 35 incorporated into the microcontroller 100. User input signals 55 to the microcontroller 100 are sent through optoisolators 60 to isolate the input signals from the microcontroller's voltage which is relative to the negative portion of the AC input power voltage. The sensor interface 25 includes circuitry to convert the 0-5 VDC or 4-20 mA continuous signals into a Pulse Width Modulated (PWM) signal that passes through the optoisolators 60 and is conditioned back into the 0-4.3V for protection from analog device signal over-voltages.

The remote user interface UI 45B may be hardwired to the remote interface circuit 20 using standard eight wire network cable (e.g., CAT 5.) In an alternate embodiment, a wireless arrangement based on BlueTooth (TM) or the various IEEE standards 802.11x, where x denotes the various present and evolving wireless computing standards may be used to connect the remote user interface UI 45B to the microcontroller 100. The optoisolators 60 ensure that only low voltage DC is provided to the remote interface unit 45B as a user electrical shock prevention safety feature.

The various external devices 30A,B,C 105, 120, 125, 130 include in one embodiment, first and second electronic ballast circuits 105, 110 which are coupled to first and second gas discharge lamps 110, 115. The first and second electronic ballast circuits 105, 120 utilize commercially supplied electronic ballast chips available from a variety of manufacturers. For example, suitable electronic ballast chips are available from International Rectifier, Inc.; www.irf.com, nos. IR2156 and IR21593. Information concerning the IR2156 electronic ballast chip is provided in International Rectifier's Data Sheet No. PD60182-I entitled, "IR2156(S) & (PbF) Ballast Control IC," which is herein incorporated by reference. Information concerning the IR21593 electronic ballast chip is provided in International Rectifier's Data Sheet No. PD60194_A "IR21593 Dimming Ballast Control IC."

These electronic ballast chips are electrically programmable to control a wide variety of operating characteristics of the gas discharge lamps 110, 115. For example, the dead-time, run frequency, preheat frequency, preheat time, ignition current and related programmable parameters may be incorporated into the electronic ballast circuits 105, 120 by judiciously selecting the proper capacitances required to obtain the necessary RC time constants to suit a particular gas discharge lamp.

In an embodiment, the first gas discharge lamp 110 is a 185 nanometer ozone generation lamp. The ozone generation lamp 110 is a hot filament type lamp which is configured to maximize ozone generation is electrically dimmable with a 0-5V control signal 50 sent by the microcontroller 100 to the first electronic ballast circuit 105.

In an embodiment, the second gas discharge lamp 115 is an ultraviolet biocide lamp 115. The biocide lamp 115 is likewise a hot filament type lamp which is configured to irradiate a recirculated air volume sufficiently to destroy airborne pathogens. The biocide lamp 115 provides an output flux of about 300 microwatts per square centimeter when measured at one meter from the lamp. The biocide lamp(s) 115 are generally operated in an ON/OFF mode (state) and is controlled by the microcontroller 100 in dependence on detected airflow signals received by the airflow sensor 130.

The ground isolated direct voltage and current data are directly related to the operational state of the gas discharge lamps 110, 115. In the case of the ozone generation lamp 110, the voltage across the entire ozone generation lamp 110 (i.e., filaments as well as an ignition arch length) is used to produce a dynamic voltage signal 55 which is directly proportional to the ozone generation lamp's voltage.

As the ozone generation lamp 110 is dimmed, the vapor inside the ozone generation lamp 110 cools causing the lamp's internal resistance to increase. The increase in the lamp's internal resistance causes a directly proportional increase in the lamp's voltage in accordance with Ohms Law. This voltage signal 55 is measured by the microcontroller 100 to determine and control the operational state of the ozone generation lamp 110 allowing the microcontroller 100 to dim the ozone generation lamp 110 safely over a wide range of ozone demands, dynamic environmental conditions and lamp operating ages.

The microcontroller 100 controls the ozone generation lamp 110 to protect the filaments while allowing the ozone generation lamp 110 to be dimmable in conjunction with a dimmable electronic ballast circuit 105. At initial startup, the ozone generation lamp 110 is provided with a sufficient filament preheat time (controlled by the electronic ballast circuit 105) then set to full (100%) output by the microcontroller 100 for approximately thirty seconds to allow the ozone generation lamp 110 time to come up to full operating temperature before it is dimmed by the microcontroller 100. The voltage across the entire ozone generation lamp 110 is monitored continuously as the ozone generation lamp 110 is slowly dimmed to its lowest sustainable output level.

If a voltage reading is detected which is significantly higher (i.e., a voltage excursion) than two previous voltage readings, the microcontroller 100 determines that the ozone generation lamp 110 is about to go out and sends a signal to the electronic ballast circuit 105 to turn the ozone generation lamp 110 on at full (100%) output. The voltage excursion readings decrease over time due to aging effects of the lamp's filaments. In practice, the voltage changes become less prominent when compared to a newer lamp. In an embodiment, the microcontroller is programmed to compensate for the decreased voltage signal based on the run time of each lamp.

The microcontroller 100 then sends a signal to the electronic ballast circuit 105 to begin dimming the ozone generation lamp 110 once again, while increasing the lowest dimmable setting. In this manner, over many cycles, the microcontroller 100 increases the lowest dimmable setting until the lowest possible output intensity has been determined for the given air temperature and air flow. Since air temperature and air flow change continuously, the dim point is cleared and found again every fifteen minutes. Dimming of the ozone generation lamp 110 is accomplished by the microcontroller 100 sending a 0-5V signal to the first electronic ballast circuit 105.

In an embodiment, the ozone generation lamp 110 may be operated in a continuous ozone concentration monitoring mode. In this mode, the microcontroller 100 receives an analog 4-20 mA signal or a 0-5V signal from the ozone sensor 125. In this continuous ozone concentration monitoring mode is initiated by a user pressing a pushbutton 47 on the remote user interface 45B. A low ozone concentration corresponds to 0.03 parts per million (PPM), a medium ozone concentration corresponds to 0.05 PPM and a high corresponds to 0.08 PPM. These ozone setpoints are included as part of the predetermined control parameters used by the microcontroller 100 to control the ozone generation lamp 110.

In this embodiment, the microcontroller 100 receives the ozone concentrations and averages the current ozone concentration with the previous two readings to calculate how much of an increase or decrease in the ozone generation lamp intensity is required to maintain the desired ozone level. In the event that the ozone generation lamp 110 has been dimmed as much as possible to maintain an operational state, and after three consecutive readings where the measured ozone output is still above the desired level setpoint, the microcontroller 100 sends a signal to the electronic ballast circuit 105 to turn off the ozone generation lamp 110 until the measured ozone concentrations falls below the desired concentration.

In an embodiment, the ozone generation lamp 110 may be operated in a manual mode. The manual mode bypasses signals from the ozone sensor 125 if installed. In this mode, the user presses a button 47, 49 to set the ozone generation lamp 110 into a low, medium, high or boost level. The low level corresponds to an average lamp output level of approximately 25%. The 25% average output level is maintained by the microcontroller 100 by cycling the ozone generation lamp 110 on and off every few minutes at a 50% output intensity; the lowest possible dim state that the ozone generation lamp 110 can be safely dimmed without risking possible damage to the lamp.

The medium level corresponds to an output level of approximately 50%. When dimming to about the 50% intensity level, the microcontroller 100 programmatically controls the lamp output intensity so that the minimum lamp output level stays above the voltage excursion point described above. When dimming to about the 75% intensity level, the microcontroller 100 first determines where the approximate 50% intensity level is situated, given the current air flow, air temperature and lamp age. Once the voltage excursion threshold has been determined, the microcontroller calculates the required dimming level to achieve the 75% intensity level. The boost mode corresponds to a 100% output intensity and is achieved by the user continuously depressing the pushbutton 47 on the user interface 45B for a few seconds, at which point the ozone generation lamp 110 is set at 100% output for 30 minutes before it returns to the previous setting.

In an embodiment, the ozone generation lamp 110 may be operated in relay signal monitor mode. In this mode, the microcontroller 100 receives a switch (state) signal from the ozone sensor 125. In this embodiment, the desired ozone concentration setpoint is set on the ozone sensor. When the ozone concentration rises above the desired ozone concentration level the switch opens, or alternately, when the ozone concentration falls below the desired concentration level the switch closes.

In this embodiment, the microcontroller 100 programmatically seeks the closed state. When the microcontroller 100 senses that the switch is closed, the microcontroller 100 slowly increases the ozone generation lamp 110 output level until the switch opens. Upon detecting the change in the switch state, the microcontroller 100 slowly decreases the ozone output level. As discussed above, if the ozone generation lamp 110 is dimmed to the minimum sustainable operational level and the switch is still open, then the microcontroller 100 will turn the ozone generation lamp 100 off until the switch opens.

The ozone generation lamp 110 is controlled by the microcontroller 100 to minimize the number of cold restarts which deteriorates the filaments within the lamp. The prolonged life of the ozone generation lamp 110 reduces maintenances costs and minimizes hazardous waste generation.

In the case of the biocide lamp 115, the electronic ballast circuit 120 monitors the voltage across a bottom filament of the biocide lamp 115. In a preheat mode, the amount of current passing through the lamp's filaments are fixed, thus allowing the voltage across the filament to be directly proportional to its resistance. The lamp's filament resistances are a function of their temperatures. As such, the biocide lamp 115 is allowed a sufficient amount of time to warm up and only ignite the lamp when the lamp's filaments have reached their ideal operating temperatures as recommended by the lamp's manufacturers. The microcontroller 100 determines the operating state of the biocide lamp 115 by measuring changes in voltage which are directly proportional to the filament's resistance. As the lamp's filament's warm up, the filament's resistance increases dramatically, approximately three fold, allowing the microcontroller 100 to measure the proper point in which to ignite the lamp. This ability to minimize the impact of cold starts on the lamp's filaments and ensuring that the lamp's filaments are not under or overheated regardless of the dynamic environmental conditions, thus prolonging the biocide lamp's 115 operational life, reducing maintenances costs and minimizing hazardous waste generation.

An ozone sensor 125 is provided to measure the ambient ozone concentration contained in the recirculated air volume. The microcontroller 100 may be configured to receive three different types of signals from the ozone sensor 125 including continuous analog signals (0-5V, 4-20 mA) or binary relay state signals (ON/OFF). The ability to utilize several different signal types provides greater flexibility in the number and types of ozone sensors 125.

An airflow sensor 130 is provided to detect the presence of air flow in the HVAC system. The microcontroller 100 is programmed to turn off the ozone and biocide lamps 110, 115 if the air flow falls below a predetermined setpoint indicative of the HVAC system being turned off. This feature minimizes electrical power usage and prolongs the operational life of the two lamps 110, 115. The airflow sensor may be adjusted to control a gas discharge lamp at various thresholds to compensate for variations in HVAC systems or dynamic variations in airflow within the HVAC system.

Figure 2:
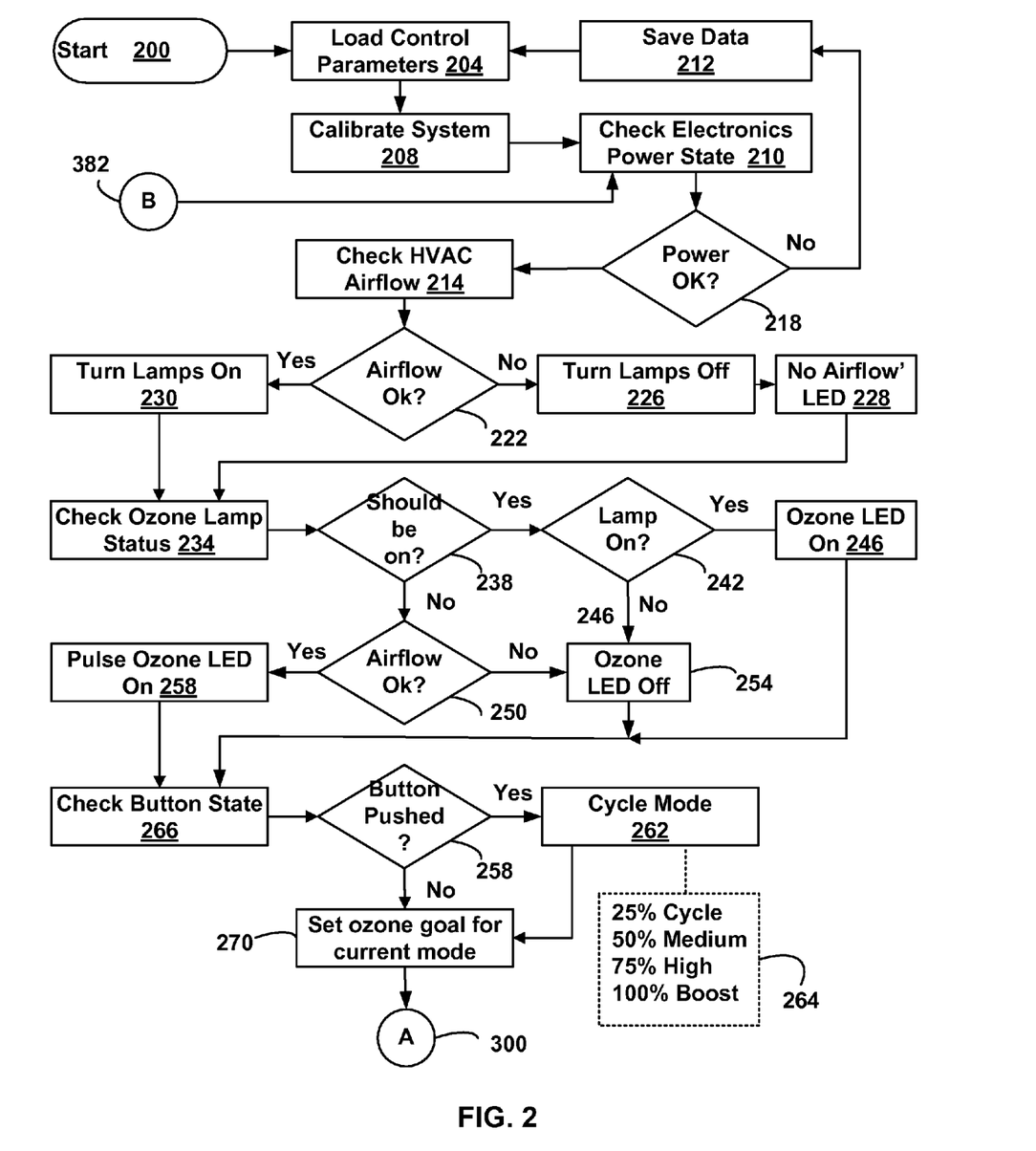
FIG. 2—depicts an exemplary flow chart of a process for intelligently controlling the operation of an ozone generation lamp.

Referring to FIG. 2, an exemplary flow chart of a programmatic process for intelligently controlling the operation of an ozone generation lamp 110 is depicted. Where necessary, the firmware programs, applications, algorithms and routines may be programmed in a high level language, for example JAVA (TM), C++, C#, or BASIC. Alternately, assembly language specific to the microcontroller may be used. An exemplary computer code provided in a version of BASIC is provided in Appendix 1 to this specification. Appendix 1 is hereby incorporated by reference in its entity as if fully set forth herein.

The process is initiated 200 by loading the control parameters 204 from memory followed by a system calibration 208. The microcontroller then checks the power status of the power supply 210. If the power state is abnormal (i.e., and undervoltage state or a failed state) 218, the microcontroller goes into fault mode where it saves the critical data in non-volatile memory 212. If the power state is normal 218, the microcontroller checks whether there is airflow in the HVAC system 214.

If a low airflow or no air flow state is determined from the airflow sensor 222, the microcontroller sends a signal to the electronic ballast circuit 1 and electronic ballast circuit 2 to turn off the ozone generation lamp and the biocide lamp 226 and indicates a no airflow state on the display LED 228.

If the airflow is determined to be normal 222, the microcontroller checks the operational status of the ozone generation lamp 234. If the ozone generation lamp is programmatically permitted to be on 238 (i.e., the ozone concentrations have not been determined to be too high) and the ozone generation lamp is indeed on 242, then the display LED will indicate that the ozone generation lamp is on 246. If the ozone generation lamp is programmatically permitted to be on 238 and the ozone generation lamp is off 242, then the display LED will indicate that the ozone generation lamp is off 254. If the ozone generation lamp is not programmatically permitted to be on 238, and there is airflow 250 then the display LED indicates that the ozone generation lamp is shutoff programmatically by pulsing the ozone generation lamp LED 258. If the ozone generation lamp is not programmatically permitted to be on 238, and there is no airflow 250 then the display LED indicates that the ozone generation lamp is off 254.

The microcontroller then checks the user interface button 266. If the button has been pushed 258, the unit's operating mode is cycled 262. The microcontroller then sets the ozone concentration threshold to what the ozone sensor should ideally read for the current operating mode 270.

In an alternate exemplary embodiment, the microcontroller does not read a signal from the ozone analyzer. In this embodiment, the ozone generation lamp may be cycled on and off at approximately 50% output to produce a 25% output low level, set to 50% output for medium level, set to 75% for a high level, and 100% for boost level 264. In this embodiment, the user selects the ozone level by pressing the button the user interface 266 to set the appropriate operating mode.

Figure 3:
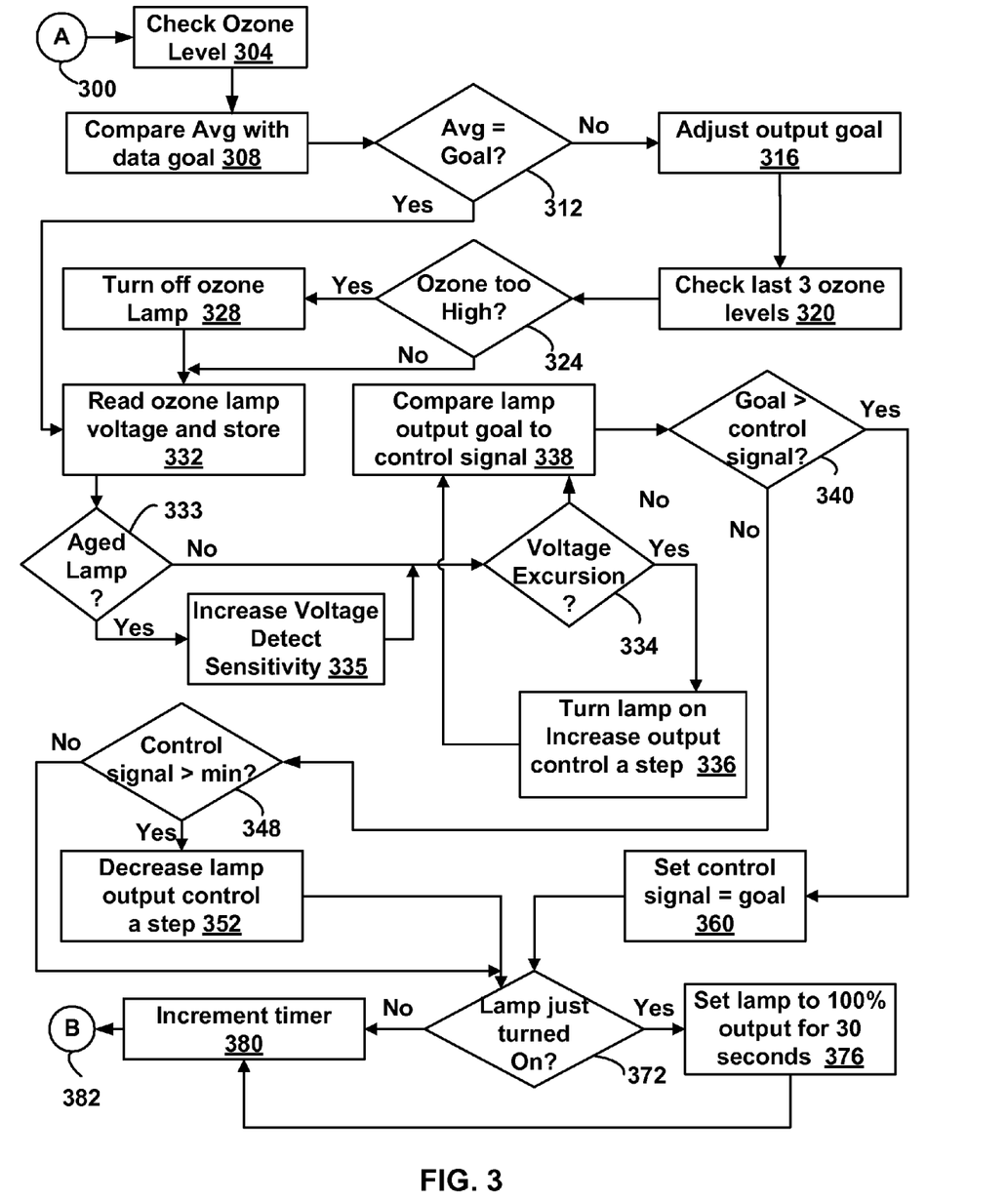
FIG. 3—depicts a continuation of the exemplary process for intelligently controlling the operation of the ozone generation lamp.

The 75% level is found by first searching for the 50% level given the particular environmental conditions, then calculating the appropriate 75% output level as is described below in the process for intelligently controlling the dimming of the ozone generation lamp 332 (FIG. 3).

The process continues at A 300 of FIG. 3. Continuing at A 300 of FIG. 3, the microcontroller reads the current ozone level from the ozone sensor 304 and averages the current ozone concentration reading with the two previous readings. The microcontroller then compares the current average to the ideal ozone concentration threshold previously set 308.

If the current average does not equal the ideal ozone concentration threshold 312, the ozone output goal is adjusted up or down 316 as appropriate by the microcontroller to return the ozone concentration to an operating band defined by the preestablished control parameters.

If the microcontroller has dimmed the ozone generation lamp as far as it can safely be dimmed (approximately 50%) and the last three ozone measurements 320 were above the desired operating band 324 for the given mode, the microcontroller turns the ozone generation lamp off and prevents the lamp from turning on until the ozone measurement drops below the operating band for the given mode 328.

The microcontroller begins a process for intelligently restarting and controlling the dimming of the ozone generation lamp. The microcontroller reads the current lamp voltage 332, stores the current voltage reading in memory and determines whether the age 333 of the ozone generation lamp exceeds one or more of the predetermined control parameters 204 (FIG. 2.) The microcontroller is programmed to compensate for aging of the ozone generation lamp by keeping track of the hours of operation, essentially by a counter, for example, the service counter 380.

If the age of the ozone generation lamp 333 exceeds the one or more predetermined control parameters 204, the voltage detection sensitivity is increased 335 to allow the microcontroller to detect a smaller voltage excursion 334 as is discussed below. The microcontroller continuously monitors the voltage across the lamp's filaments until a voltage excursion is detected 334 as is discussed below. Such an excursion is indicative of the ozone generation lamp about to go out. The microcontroller uses the current voltage reading and two previous readings to determine if there has been an excursion.

If a voltage excursion has occurred, the ozone generation lamp is turned on and the output control signal is increased by a step 336. The microcontroller then compares the control signal to the output goal 338. If the goal is larger than the control signal 340 then the control signal is set equal to the goal 360 and the microcontroller exits the current loop and proceeds to determine if the ozone generation lamp has just turned on 372 as is described below.

If the goal is less than the control signal 340 then the microcontroller compares the control signal to the minimum allowable control value 348. If the control signal is greater than the minimum allowable control value 348 then the control signal is decreased by a step. Each control step is determined by the number of bits available to the processor. In this exemplary embodiment, an 8 bit processor is employed; therefore a total of 256 voltage steps are available. In this exemplary embodiment, each step corresponds to +/−0.02V (0-5V control signal range/256 bits.) Then the microcontroller exits the current loop and proceeds to determine if the ozone generation lamp has just turned on 372 as is described below.

If the microcontroller determines that the ozone lamp has just turned on 372, the microcontroller sends a signal to the electronic ballast circuit to set the output to 100% for thirty seconds to allow the ozone generation lamp to fully warm up 376. The microcontroller then increments the service timer 380 and returns to the beginning of the loop at B 382 of FIG. 2.

Figure 4:
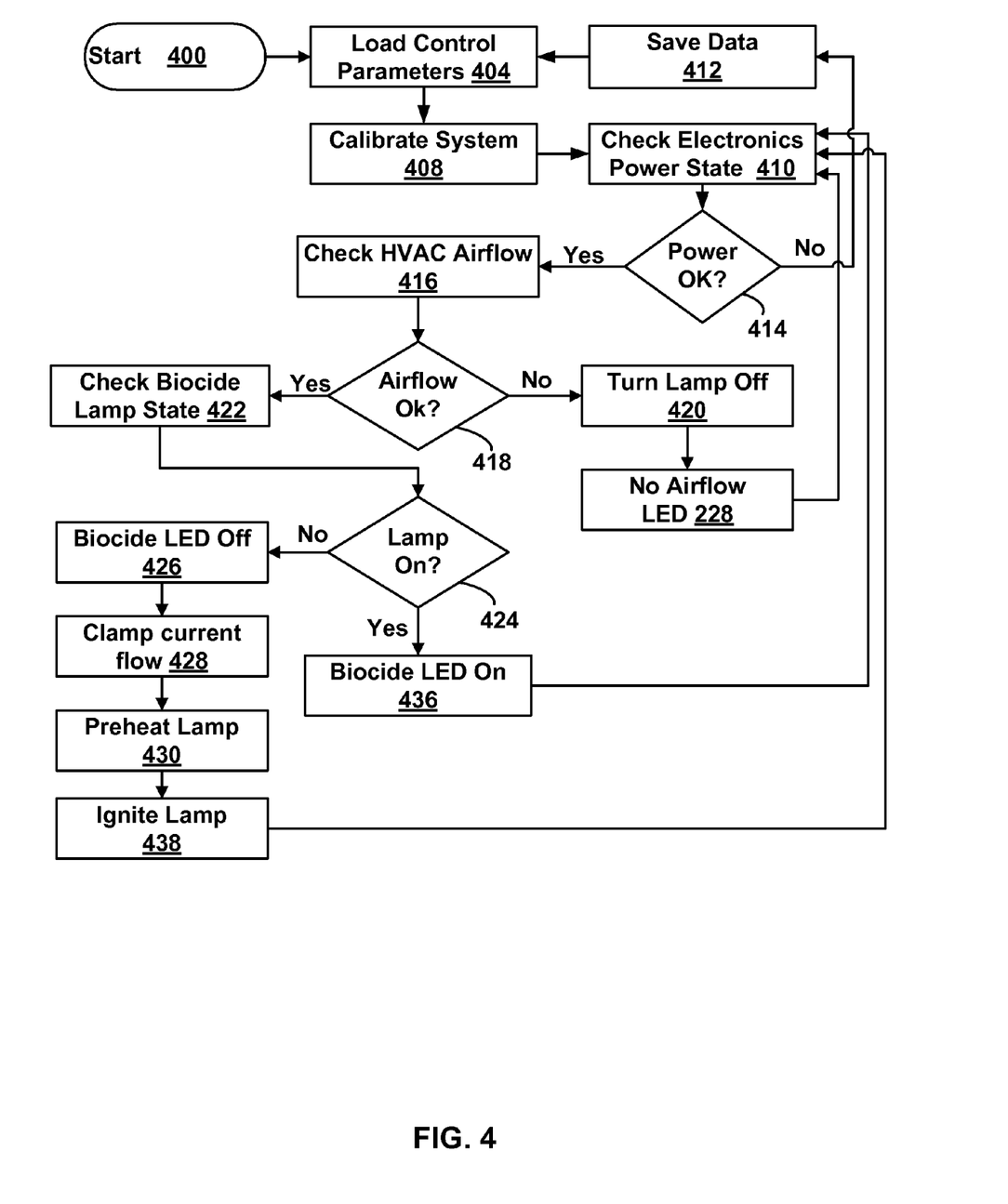
FIG. 4—depicts an exemplary flow chart of a process for intelligently controlling the operation of a biocide lamp.

Referring to FIG. 4, an exemplary flow chart of a programmatic process for intelligently controlling the operation of the biocide lamp is depicted. Unlike the ozone generation lamp, the biocide lamp is generally operated in a continuous full power mode except during initial startup, maintenance, power failures and HVAC airflow loss.

The process is initiated 400 by loading the control parameters 404 from memory followed by a system calibration 408. The microcontroller then checks the power status of the power supply 410. If the power state is abnormal (i.e., an undervoltage state or a failed state) 414, the microcontroller goes into fault mode where it saves the critical data in non-volatile memory 412. If the power state is normal 414, the microcontroller checks whether there is airflow in the HVAC system 416.

If a low airflow or no air flow state is determined from the airflow sensor 418, the microcontroller sends a signal to the electronic ballast circuit 1 and ballast circuit 2 to turn off both the ozone generation lamp and the biocide lamp 226 and indicates a no airflow state on the display LED 228.

If the airflow is determined to be normal 418, the microcontroller checks the operational status of the biocide lamp 422. If the biocide lamp is actually on 424, the biocide lamp LED is turned on 436 and the process repeats in a loop 410 by repeatedly checking the power state 410, HVAC airflow 416 and biocide lamp state 418.

If the biocide lamp is not turned on 424, the biocide lamp LED is turned off 426, the microcontroller signals the electronic ballast circuit for the biocide lamp to turn on the lamp while maintaining a constant current across the lamp's filaments 428 during the preheating of the biocide lamp 430. The microcontroller continuously monitors the voltage across the biocide lamps' filaments until the biocide lamp has obtained a sufficient operating temperature to ignite the vapor within the lamp 438. Once the biocide lamp is ignited, the process repeats in the loop 410 by repeatedly checking the power state 410, HVAC airflow 416 and biocide lamp state 418 as previously described.

The various exemplary embodiments described herein are merely illustrative of the principles underlying an inventive concept. It is therefore contemplated that various modifications of the disclosed exemplary embodiments will, without departing from the spirit and scope of the various exemplary inventive embodiments will be apparent to persons of ordinary skill in the art. In particular, it is contemplated that functional implementation of the various exemplary embodiments described herein may be implemented equivalently in hardware, software, firmware, and/or other available functional components or building blocks. No specific limitation is intended to a particular method, system or process sequence. Other variations and exemplary embodiments are possible in light of above teachings, and it is not intended that this Detailed Description limit the scope of invention, but rather by the Claims following herein.

What is claimed:

1. An electronic control circuit for intelligently controlling a gas discharge lamp associated with an HVAC system comprising:
    a microcontroller having operatively coupled thereto;
    a memory including instructions executable by the microcontroller to process a plurality of dynamic lamp state signals and dynamically generate control signals in at least partial dependence on a plurality of pre-established control parameters to maintain the gas discharge lamp in a minimum operable state defined by the pre-established control parameters;
    an electronic ballast circuit configured to dynamically control a current flow through the gas discharge lamp in dependence on the dynamically generated control signals; and,
    wherein the microcontroller iteratively determines the minimum operable state of the gas discharge tube in at least partial dependence on a voltage excursion included as one of the plurality of dynamic lamp state signals.

2. The electronic control circuit according to claim 1 further including an airflow sensor operatively coupled to the microcontroller and configured to provide airflow state signals to the microcontroller in dependence on airflow through the HVAC system.

3. The electronic control circuit according to claim 2 further including an ozone sensor operatively coupled to the microcontroller and configured to provide ozone sensor signals to the microcontroller in dependence on an ozone concentration in the HVAC system.

4. The electronic control circuit according to claim 3 further including a power supply configured to provide sufficient electrical power to the microcontroller, electronic ballast circuit and the gas discharge lamp in an isolated ground arrangement such that voltage measurements are relative to a negative portion of an input power sine wave.

5. The electronic control circuit according to claim 4 further including a user interface operatively coupled to the microcontroller and configured to receive user inputs to display a state of at least one of, the airflow sensor, the gas discharge lamp, the ozone sensor and the power supply.

6. The electronic control circuit according to claim 1 wherein the dynamic control signals is one of, an ON/OFF signal, a pulse width modulation signal, an output intensity signal, a user interface signal and a voltage signal.

7. The electronic control circuit according to claim 1 wherein the plurality of dynamic states of the gas discharge lamp is one of, an ON/OFF state, a preheat state, an ignition state and a dimmed state.

8. The electronic control circuit according to claim 1 wherein the dynamic lamp state signals are 0-5 volt signals measured relative to a negative portion of an input power sine wave and an isolated ground.

9. The electronic control circuit according to claim 1 wherein the plurality of pre-established control parameters is one of, an operating cycle time, an output intensity level, a service schedule time, a low ozone setpoint and a high ozone setpoint.

10. The electronic control circuit according to claim 1 wherein the gas discharge lamp is an ozone generator lamp.

11. The electronic control circuit according to claim 9 wherein the output intensity level is one of; about a 25 percent output duty cycle of the gas discharge tube in a low mode, about a 50 percent output in medium mode, 75 percent output in a high mode and 100 percent in a boost mode.

12. The electronic control circuit according to claim 9 wherein the output intensity level is incrementally adjustable by 256 discrete voltage steps.

13. The electronic control circuit according to claim 1 wherein the voltage excursion is measured relative to a negative portion of an input power sine wave and an isolated ground.

14. The electronic control circuit according to claim 12 wherein the 256 discrete voltage steps represent an output intensity range of 50%-100%.

15. The electronic control circuit according to claim 12 wherein the output intensity may be dynamically controlled at output levels below 50% by pulsing of the gas discharge lamp.

16. The electronic control circuit according to claim 1 wherein the instructions executable by the microcontroller further includes instructions to adjust a voltage excursion detection sensitivity in at least partial dependence one or more of the plurality of pre-established control parameters.

17. An electronic control circuit for intelligently controlling a pair of gas discharge lamps associated with an HVAC system comprising:
    a microcontroller having operatively coupled thereto;
    a memory including instructions executable by the microcontroller to dynamically generate control signals in at least partial dependence on a plurality of optically isolated input signals;
    a first electronic ballast configured to control a first current flow through an ozone generation lamp in dependence on a portion of the dynamically generated control signals;
    a second electronic ballast configured to control a second current flow through a biocide lamp in dependence on another portion of the dynamically generated control signals;
    a power supply operatively coupled to the microcontroller, the first electronic ballast and the second electronic ballast; the power supply including a separate isolated ground having a different voltage potential from a common ground.

18. The electronic control circuit according to claim 17 wherein the plurality of optically isolated input signals includes voltage signals, current signals, airflow state sensor signals and ozone sensor signals.

19. The electronic control circuit according to claim 17 wherein the plurality of input signals includes a voltage signal derived from an operational state of the power supply.

20. The electronic control circuit according to claim 18 wherein the airflow sensor is configurable to control one of, the biocide lamp, ozone generation lamp and any combination thereof in dependence on various airflow thresholds included in one or more of the plurality of pre-established control parameters to compensate for dynamic air flow variations.

21. An electronic control circuit for intelligently controlling a pair of disparate gas discharge lamps associated with an HVAC system comprising:
a microcontroller having operatively coupled thereto;
a memory including instructions executable by the microcontroller to process a plurality of input signals and dynamically generate control signals for each of the gas discharge lamps in at least partial dependence on a plurality of pre-established control parameters to maintain the gas discharge lamps in states defined by the pre-established control parameters;
a first electronic ballast circuit configured to control a current flow through either an ozone generation lamp or a first biocide lamp in at least partial dependence on voltage dependent control signals received from the microcontroller; and,
a second electronic ballast circuit configured to control a current flow through a second biocide lamp in at least partial dependence on the voltage dependent control signals received from the microcontroller.

22. The electronic control circuit according to claim 21 the plurality of input signals includes airflow state signals, ozone sensor signals, current signals, voltage signals and ON/OFF state signals.

23. The electronic control circuit according to claim 22 wherein the dynamically generated control signals associated with the ozone generation lamp is generally dependent on the ozone sensor signals.

24. The electronic control circuit according to claim 22 wherein the voltage dependent control signals comprises a ground isolated 0-5V signal measured relative to a negative portion of an input power sine wave and the isolation ground.

25. The electronic control circuit according to claim 22 wherein the dynamically generated control signals derived from the airflow state signals controls both the ozone generation lamp and the first biocide lamp.

26. The electronic control circuit according to claim 22 wherein the ON/OFF state signals is associated with either a relay state or a user interface switch.

27. The electronic control circuit according to claim 21 wherein the ozone generation lamp is iteratively controlled by the microcontroller to maintain operation at a lowest possible operating intensity in at least partial dependence on the plurality of input signals.

28. The electronic control circuit according to claim 21 wherein the microcontroller ignites the biocide lamp only after a sufficient warm-up period in dependence on a significant increase in resistance across a filament associated with the biocide lamp using an electronic ballast circuit lacking an internal dimming circuit.

* * * * *